(12) United States Patent
McEwen

(10) Patent No.: US 6,531,241 B1
(45) Date of Patent: Mar. 11, 2003

(54) CYCLIC DELOCALIZED CATIONS CONNECTED BY SPACER GROUPS

(75) Inventor: Alan B. McEwen, Melrose, MA (US)

(73) Assignee: Covalent Associates, Inc., Woburn, MA (US)

( * ) Notice: Subject to any disclaimer, the term of this patent is extended or adjusted under 35 U.S.C. 154(b) by 0 days.

(21) Appl. No.: 09/611,787

(22) Filed: Jul. 7, 2000

Related U.S. Application Data

(60) Provisional application No. 60/142,726, filed on Jul. 8, 1999.

(51) Int. Cl.[7] .............................. H01G 9/00; H01G 1/74; H01M 8/14; H01M 4/60
(52) U.S. Cl. .................. 429/46; 429/212; 429/213; 361/500; 361/503; 361/504; 252/62.2; 252/500
(58) Field of Search .................. 508/221; 252/62.2, 252/500; 429/46, 212, 213; 361/500, 503, 504

(56) References Cited

U.S. PATENT DOCUMENTS

| | | | |
|---|---|---|---|
| 4,758,671 A | 7/1988 | Dvorsk et al. | 548/341 |
| 5,827,602 A | 10/1998 | Koch et al. | 429/194 |
| 5,870,275 A | 2/1999 | Shiono et al. | 361/504 |
| 5,965,054 A | 10/1999 | McEwen et al. | 252/62.2 |

FOREIGN PATENT DOCUMENTS

| | | | |
|---|---|---|---|
| WO | WO 00/32572 | 6/2000 | 213/0 |
| WO | WO 00/32658 | 6/2000 | 210/8 |

OTHER PUBLICATIONS

*Separation of Sublethal and Lethal Effects of the Bactericidal/Permeability Increasing Protein on Escherlchla coli*; Brian A. Mannion, et al., Steps in Bacterial Killing by a Neutrophil Cytotoxin, XP–002159676, pp. 853–860.

Kaori Ito, et al., Enhanced ion conduction in imidazolium–type molten salts; Electrochimica Acta 45(2000), 1295–1298.

Michiko Hirao, et al., Preparation and polymerization of new organic molten salts; N–alkylimidazolium salt derivatives; Electrochimica Acta 45 (2000), 1291–1294.

Hiroyiki Ohno, et al., Ionic Conductivity of Molten Salts Formed by Polyether/salt Hybrids; Chemistry Letters, 1998, pp. 15 ff.

Pilar Cabildo, et al., Positive Ions and Negative Ions FAB (Fast Atom Bombardment) Mass Spectrometry of some Bisazolium Salts; J. Heterocyclic Chem., 34. 367 (1997).

Rosa Maria Claramunt, et al., (N–Polyazolyl)methanes. II. Synthese et reactivite de methylene–1,1' dipyrazoles. Bulletin de la Societe Chimique de France, 1983, No. 1–2.

Rosa Maria Claramunt, et al., N–Polyazolylmethanes. III. [I]. Synthese et etude rmn du proton des derives du methylene–1,1' diimidazole et du methylene–1,1' dibenzimidazole. J. Heterocyclic Chem., 20, (1983), 1245.

Volke, J., et al., Comproportionalion in the reduction of pyridinium derivatives –a combined ESR and electrochemical study; Electrochimica Acta, vol. 42, No. 12, pp. 1771–1780; 1997.

*Primary Examiner*—Jacqueline V. Howard
(74) *Attorney, Agent, or Firm*—Weingarten, Schurgin, Gagnebin & Lebovici LLP

(57) ABSTRACT

Cyclic delocalized cations joined together by spacer groups, with anions of equal number to cations to maintain charge neutrality, are disclosed. These spacer groups may be organic or inorganic in origin and may vary in length. The spacer groups may be saturated, containing single bonds, or may be unsaturated, containing double and triple bonds. With appropriate design these materials can have melting and glass transition temperatures below, around, and above room temperature. The lyophobic character of these materials may be adjusted, providing unique properties. These materials are well suited for use as electrolytes, lubricants, solvents for extractions and for running reactions, biphase catalysis media, media for electroluminescent devices.

13 Claims, 3 Drawing Sheets

Pyridinium

Pyridazinium

Pyrimidinium

Pyrazinium

Imidazolium

Pyrazolium

Thiazolium

Oxazolium and

Triazolium

CYCLIC DELOCALIZED CATIONS CONNECTED BY SPACER GROUPS

CROSS REFERENCE TO RELATED APPLICATIONS

This application claims priority of U.S. Provisional Application No. 60/142,726, filed Jul. 8, 1999, entitled CYCLIC DELOCALIZED CATIONS CONNECTED BY SPACER GROUPS, the whole of which is hereby incorporated by reference herein.

FIELD OF THE INVENTION

This invention deals with cyclic delocalized cations joined together by spacer groups, with anions of equal number to cations to maintain charge neutrality. These materials are well suited for use as electrolytes, lubricants, solvents for extractions and for running reactions, biphase catalysis media, and immobilizing ionic media for electroluminescent and electrochromic devices.

BACKGROUND OF THE INVENTION

There has been limited disclosure of compounds containing two or more delocalized cations, and none have disclosed the utility of the compounds as electrolytes, lubricants, solvents, etc.

Acerete et al. (Revue Roumaine de Chimie, 36 (1991) 629) disclose the neutral bisazolyl compounds with one or two methylene spacer groups between the ring structures. They investigated the proton acidity of the neutral compounds.

Claramunt, Elguero, and Meco (J. Heterocyclic Chem., 20 (1983) 1245) disclose the NMR characteristics of bisimidazole compounds with one methylene group as a spacer and the bisimidazolium salts with halides as the counter anion.

Claramunt, Hernandez, et al. (Bull. De la Societe Chemique de France (1983) II-5) disclose the synthesis of bispyrazole compounds with one methylene group as a spacer and the bispyrazolium salts using fluorosulfaonate ($FSO_3^-$) as the counter anion.

Ohno, Nakai, and Ito (Chemistry Letters (1998)15) disclose the use of polyethylene oxide linked sulfonamide anions for use as lithium polymer electrolytes. They teach that by mixing these bis-sulfonamide anions with the bromo imidazolium cations having polyethylene oxide side chains the ionic conductivity is improved.

Torres et al. (Bull. Soc. Chim. Belg., 101 (1992) 29) disclose the synthesis and NMR characteristics of the salts resulting from 1,2-bisazolylethanes and 1,2-bisbenzazolylethanes having fluorosulfonate ($FSO_3^-$) or sulfate ($SO_3^{2-}$) as the counter anions. These biscation materials have high melting points, in some cases well above 300° C.

Cabildo et al. (J. Heterocyclic Chem. 34 (1997) 367) disclose the mass spectrometry of bisimidazolium and bispyrazolium salts with one and two methylene spacer groups between the two cations and with halides (iodide, bormide, or chloride) or $SO_4H^-$ as the counter anion. They teach the advantage of using Fast Atom Bombardment in determining the structural information of these salts.

There has been disclosure of divalent imidazolium compounds in general (see e.g. Murphy, Publication WO 00/32658 (application PCT/US99/28740)). However, this publication does not distinguish between the various divalent compounds in terms of thermal and electrochemical stability and phase transition characteristics. In addition, the publication deals with the use of these compounds as components in the polymerization of isoolefins, particularly poly-isobutylenes.

BRIEF SUMMARY OF THE INVENTION

This invention deals with cyclic delocalized cations joined together by spacer groups, with anions of equal number to cations to maintain charge neutrality. These spacer groups may be organic or inorganic in origin and may vary in length. The spacer groups may be saturated, containing single bonds, or may be unsaturated, containing double and triple bonds. With appropriate design these materials can have melting and glass transition temperatures below, around, and above room temperature. The lyophobic character of these materials may be adjusted, providing unique properties.

These materials are well suited for use as electrolytes, lubricants, solvents for extractions and for running reactions, biphase catalysis media, and immobilizing ionic media for electroluminescent and electrochromic devices.

DETAILED DESCRIPTION OF THE INVENTION

This invention deals with cyclic delocalized cations joined together by spacer groups, with anions of equal number to cations to maintain charge neutrality. FIG. 1 is a graphical depiction of chemical structures that are the subject of this invention. The circle and + represents a cation comprised of a cyclic stabilized ring structure. The bold line connecting these cations depicts a linking group comprised of a polymer like backbone. The anion is represented by X–, wherein the negative charge equals that of the positive charge. In the simplest form, a dication material represented by (A) is the subject of this invention. Alternatives include an extended chain of cyclic stabilized cations linked together, having anions which are not structurally connected to the backbone (see B); with tethered anions which are structurally linked to the backbone (see C); or with anions linked to each other with any linking group (see D), thus forming separate linear or branched chains of anions and cations.

Figure 3:
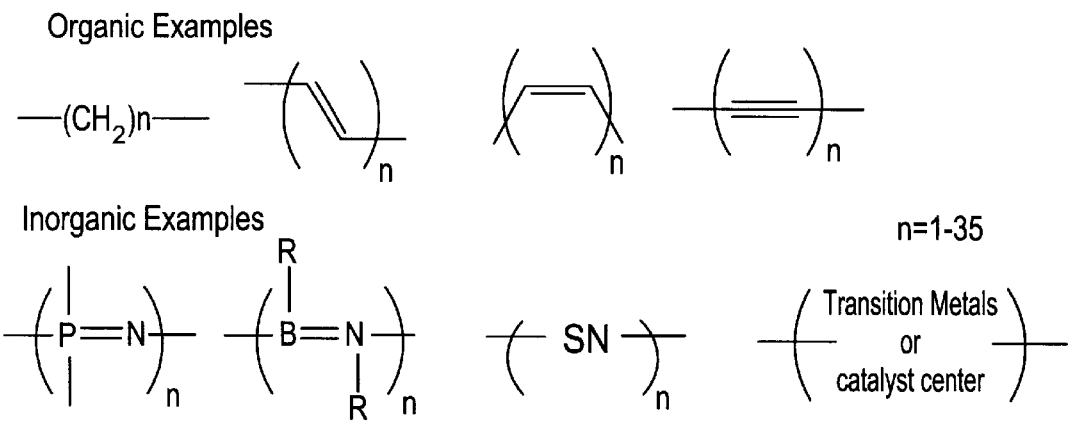
FIG. 3 represents examples of the linking group (also referred to as spacer group), which may be thought of as a chain or polymer unit connecting the cations.

These spacer groups (also referred to as linker groups) may be organic or inorganic in origin and may vary in length and preferably contain 1–35 monomer units. The spacer groups may be saturated, containing single bonds, or may be unsaturated, containing double and triple bonds. FIG. 3 represents examples of the linking group, which may be thought of as a chain or polymer unit connecting the cations. The linking group may be organic and or inorganic in nature. Examples of organic groups are the methylene, olefin, and alkyne hydrocarbon repeating units. Other alternatives of the linking group are that the repeating unit comprises a standard polymer such as polyethylene oxide, polyacrylonitrile, polyesters, polyamides, polyvinyl chloride, polypropylene and other polymer units. Inorganic chain examples can be sulfur nitride or polythiazyl, borazine type structure, or a transition metal or metal cluster. Other possible polymer units are silicates, titanates, polythiophene, and other such structures known to those who work in the field.

With appropriate design these salts can have melting and glass transition temperatures below, around, and above room temperature. The lyophobic character of these materials may be adjusted, providing unique properties.

These materials are well suited for use as electrolytes, lubricants, solvents for extractions and for running reactions, biphase catalysis media, media for electroluminescent devices.

The materials invented herein are ionic and may be in liquid form, depending on the cationic spacing and choice of anion.

Figure 1A:
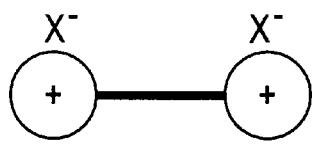
FIG. 1 is a graphical depiction of chemical structures that are the subject of this invention.
Figure 1B:
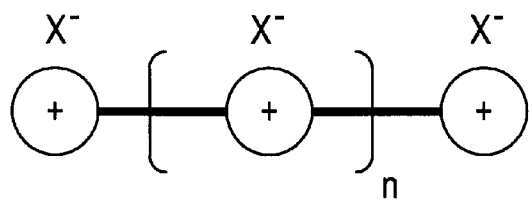
Figure 1C:
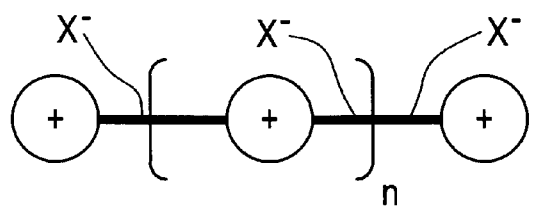
Figure 1D:
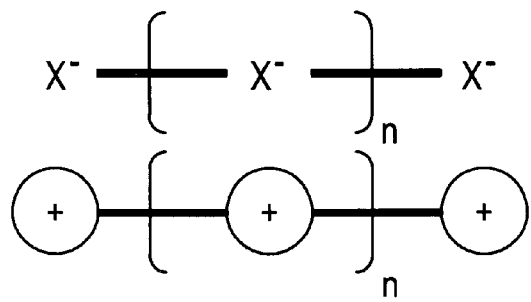
Figure 2:
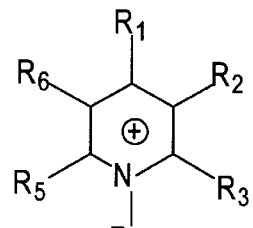
FIG. 2 are examples of cyclic stabilized cations.
Figure 2:
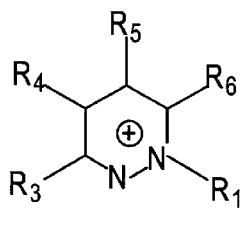
Figure 2:
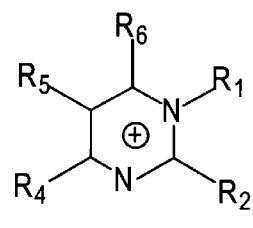
Figure 2:
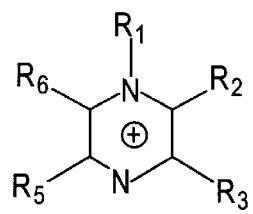
Figure 2:
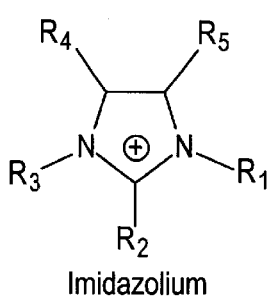
Figure 2:
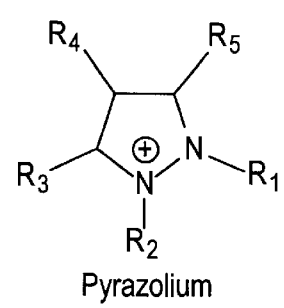
Figure 2:
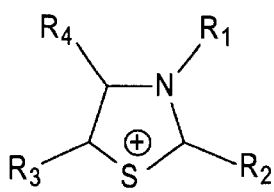
Figure 2:
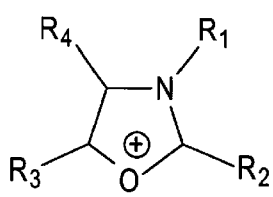
Figure 2:
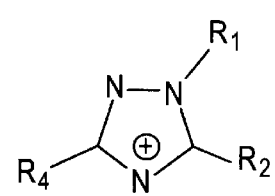
Figure 2:
Figure 4:
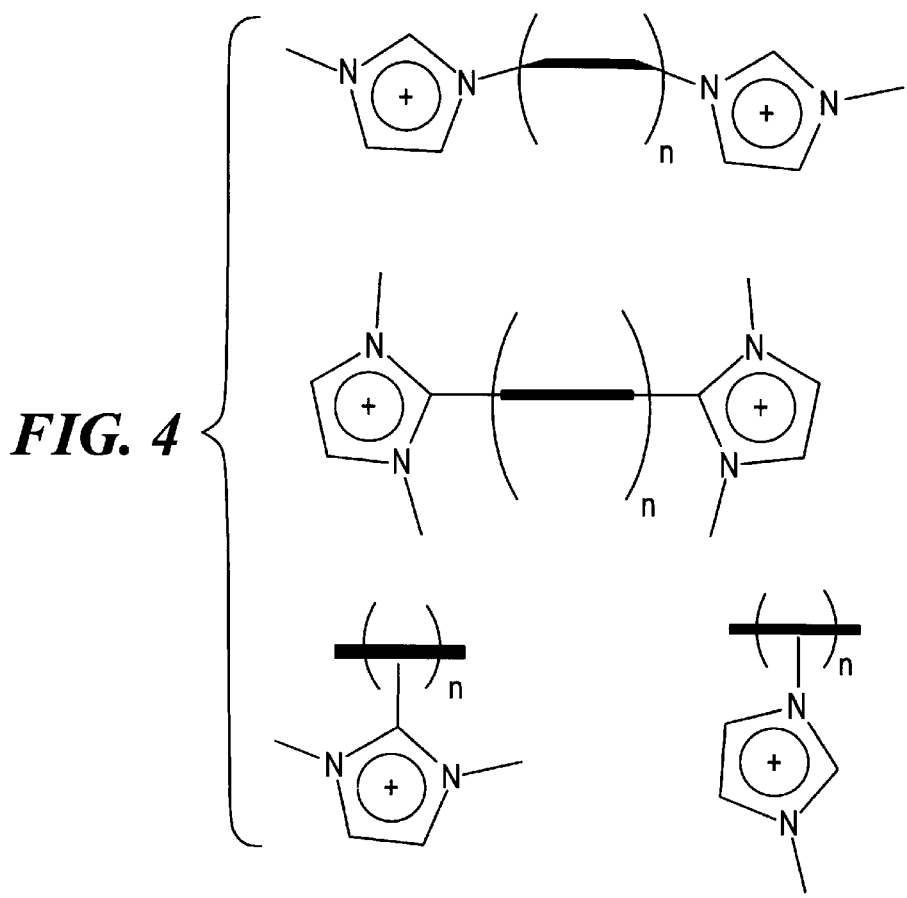
FIG. 4 represents different ways that the cations can be incorporated into the linking group backbone.

Preferably, these compounds comprise as the cyclic cations heterocyclic compounds having 5 or 6 membered rings, namely pyridinium, pyridazinium, pyrimidinium, pyrazinium, imidazolium, pyrazolium, thiazolium, oxazolium, and triazolium compounds. These cations can be incorporated with the spacer groups in various ways, as shown in FIG. 4. For example, the cations can be attached to the linker groups via the hetero atom or the carbon atom of the ring structure. As depicted in FIG. 1B, the structure may have more than two cation centers, and the cation can either be part of the linker group backbone or be a side group to the linker group backbone.

In addition, the preferred anions have been found to be bis(trifluoromethylsulfonyl)imide ("Imide" or "Im"), bis(perfluoroethylsulfonyl)imide ("Beti"), tris(trifluoromethylsulfonyl)methide ("Methide" or "Me"), the asymmetric bis(fluoroalkylsulfonyl)imide (BAI) (for example, $R=CF_3$ and $R'=C_4F_9$) and tris-(fluoroaklysulfonyl)methide (TAM), and $PF_6$, since they have been found to have unexpected thermal stability and are liquids at low temperatures, as discussed further herein.

Im=$(CF_3SO_2)_2N^-$

Methide=$(CF_3SO_2)_3C^-$

Beti=$(C_2F_5SO_2)_2N^-$

BAI=$(RSO_2)N^-(SO_2R')$

As shown in FIG. 1, the anions can exist in various ways relative to the cation chain. For example, they can exist as individual anions in solution, not structurally connected to the cation chain. Alternatively, they can exist as anions individually connected to (i.e., tethered) to the backbone, for example by linking through one of the sulfonate groups with an alkyl or other type structure. (When the anions are tethered to the cation structure, the resulting compound can be considered a zwitterionic material.) In addition, the anions themselves can form a monolithic unit linked together with assorted connecting groups. (See Ohno et al for other possible ways of linking anions.)

Thus, the preferred embodiments are salts with cations having the following structures:

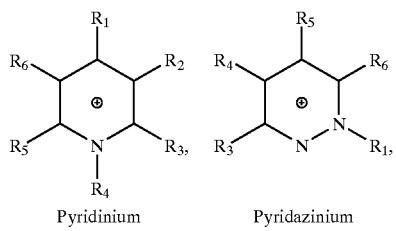

Pyridinium   Pyridazinium

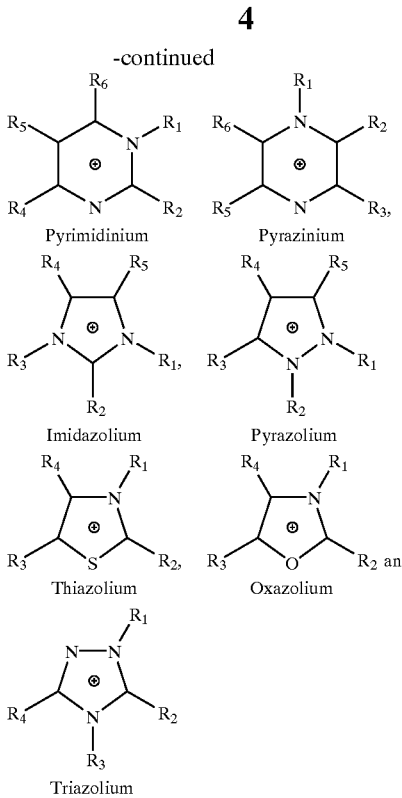

Pyrimidinium   Pyrazinium

Imidazolium   Pyrazolium

Thiazolium   Oxazolium and

Triazolium wherein $R_1$, $R_2$, $R_3$, $R_4$, $R_5$, and $R_6$ are either H, F, or separate alkyl groups, respectively, wherein at least one alkyl group of 5 or more carbon atoms is present; or any two of $R_1$–$R_6$ can be joined together to constitute a unitary alkylene radical forming one or more ring structures converging on the cyclic delocalized aromatic ring; and wherein the alkyl groups or alkylene radicals may be substituted with electron withdrawing groups, preferably F—, Cl—, $CF_3$—, $SF_5$—; $CF_3S$—, $(CF_3)_2CHS$— or $(CF_3)_3CS$—.

A preferred embodiment is a cation wherein each ring hydrogen is replaced with either an attachment to the linking group or an alkyl substituent containing 1–25 carbon atoms, resulting in there being no ring hydrogens.

It is preferred that the salts not utilize anions which both (1) are conjugate bases to Lewis acids and (2) react with moisture, possibly liberating a gaseous product. Furthermore, it is preferred that the anion have a van der Waals volume exceeding 100 Angstroms. Thus anions such as $AlX_3$, $FeX_3$ and $GaX_3$, where X is a halogen, would preferably be excluded.

It has been found that, by adjusting the spatial separation of the cations, the physical properties of the salts may be varied. In addition, by adjusting the anion identity, the lyophobic character of the salt can be modified. For example, the $BF_4$ anion is hydrophilic, while the $PF_6$ anion is hydrophobic, and the Im anion is even more hydrophobic. Furthermore, by adjusting the substitution on the cation, the hydrophobic character may be adjusted by removing the acidic ring protons.

Choice of anion also influences the melting point and liquid range of these salts. For example, salts incorporating the Im and analogous anions typically are liquids below 100° C. Using an asymmetric type imide ion (e.g., BAI) or methide (e.g., TAM) results typically with salts having the lowest melting point. It should be noted that the anions may either be all the same in one salt or a mixture of different anions may be used in a given salt.

Improved electrochemical stability towards oxidation is obtained with the preferred embodiments (e.g., Im, Beti, $PF_6$, Me, etc.) as compared to the halide and haloaluminate anions.

Further embodiments are those salts that are hydrophilic. These compounds contain anions such as $BF_4$, perfluoroalkylsulfonates, carboxylic acids, and the mono and dianions of dicarboxylic acids such as phthalic and maleic acid. These materials are preferred when used as solvents for their specific solubility and lyophilic/lyophobic interactions. For use in biphase catalysis, for example, efficient solubility of catalysts and phase separation of products can be obtained with these hydrophilic multi-cationic materials. A preferred embodiment is the materials obtained with the phthalic acid anion.

The lack of vapor pressure, the high thermal stability, and the adjustable viscosity of these compounds are well suited properties for lubrication applications. In addition, the high electrochemical stability and high ionic conductivity gives these materials properties well suited for use as electrolytes. Specifically, the lack of vapor pressure makes these materials well suited for use at high temperatures.

The compounds invented herein are sometimes referred to as "dumbell" compounds, since their structure is similar to that of a dumbell. In particular the 1,ω-biscation structures with cyclic stabilized cations at either end of a spacer group fall into this category (FIG. 1A).

Several abbreviated notations are used for these compounds. For example, when referring to compounds in which the cations are imidazolium compounds, CnX refers to the following structure:

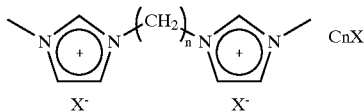

For example, C2Br refers to the compound where 2 methylene groups separate the 2 imidazole cations, linked to the spacer chain at a nitrogen group with the nitrogen at the 3-position substituted with a methyl group.

The notation $(CH_2)_2(MIBr)_2$ refers to this same compound 1,2-bis(3-methylimidazolium)ethane bisbromide. This would also have the shorthand abbreviation of C2Br as discussed previously.

The following examples are intended to further illustrate, but not limit, the invention.

EXAMPLE 1

Synthesis of 1,ω-bis(3-Methylimidazolium)alkane Molten Salts

The $(CH_2)_2(MIBr)_2$, $(CH_2)_2(MICl)_2$, $(CH_2)_3(MIBr)_2$, $(CH_2)_5(MIBr)_2$, $(CH_2)_5(MICl)_2$ and $(CH_2)_{10}(MIBr)_2$ were synthesized by refluxing the appropriate 1,ω-dibromo or -dichloro alkane with two times excess of 1-methylimidazole for 24 hours in 1,1,1-trichloroethane or toluene. The excess chloroalkane was removed by evaporation and the crude product recrystallized by dissolving in methanol and crashing out the white solid in ethyl acetate three times.

The $(CH_2)_3(MIPF_6)_2$, $(CH_2)_3(MIBeti)_2$, and $(CH_2)_5(MIBeti)_2$ salts were synthesized by stirring the appropriate lithium salt with the halide precursor in acetonitrile for three hours. The $(CH_2)_5(MIIm)_2$ was synthesized using methanol as the reaction solvent and $(CH_2)_{10}(MIPF_6)_2$ salt was synthesized with $KPF_6$ in $H_2O$ outside of the glove box.

Purity was determined by $^1H$ NMR, DSC, TGA, IR, elemental analysis (CHN and halide) and cyclic voltammetry (CV).

Characterization

Three Methylene Spacer Groups (1,3 Propane):

$(CH_2)_3(MIBr)_2$: IR (KBr pellet): 3146, 3112 and 3087 [ν(C—H) aromatic]; 2968 [ν(C—H) aliphatic]; 1637, 1568 and 1454 cm$^{-1}$ [νC=C].

$(CH_2)_3(MIBeti)_2$: IR (KBr pellet): 3171 and 3126 [ν(C—H) aromatic]; 1578 cm$^{-1}$ [νC=C].

$(CH_2)_3(MIPF_6)_2$: IR (KBr pellet): 3171 and 3126 [ν(C—H) aromatic]; 1622, 1588, 1568 and 1454 cm$^{-1}$ [νC=C]. $^1H$ NMR ($CD_3CN$, δ/ppm relative to TMS): 8.40 (m, 2H), 7.38 (dd, 2H), 7.37 (dd, 2H), 4.18 (t, 4H), 3.85 (s, 6H), 2.37 (m, 2H), 2.16 (s, 1H), 1.96 (m, 1H).

Five Methylene Spacer Groups (1,5 Pentane):

$(CH_2)_5(MIBr)_2$: IR (KBr plate): 3148 and 3092 [ν(C—H) aromatic]; 2946 and 2865 [ν(C—H) aliphatic]; 1635, 1574 and 1461 cm$^{-1}$ [νC=C]. $^1H$ NMR ($CD_3CN$, δ/ppm relative to TMS): 9.53 (m, 2H), 7.60 (dd, 2H), 7.38 (dd, 2H), 4.25 (t, 4H), 3.89 (s, 6H), 2.47 (s, 1H), 2.30, (s, 2H), 1.92 (m, 4H), 1.33 (m, 2H).

$(CH_2)_5(MICl)_2$: IR (KBr plate): 3146 and 3087 [ν(C—H) aromatic]; 2943 and 2858 [ν(C—H) aliphatic]; 1632, 1573 and 1464 cm$^{-1}$ [νC=C].

$(CH_2)_5(MIBeti)_2$: IR (KBr plate): 3159 and 3122 [ν(C—H) aromatic]; 2964 and 2875 [ν(C—H) aliphatic]; 1580 and 1472 cm$^{-1}$ [νC=C].

$(CH_2)_5(MIIm)_2$: Anal. Found (calculated): C, 26.09 (26.15); H, 2.72 (2.84); N, 10.61 (10.76). IR (KBr plate): 3161 and 3116 [ν(C—H) aromatic]; 964 and 2881 [ν(C—H) aliphatic]; 1580 and 1464 cm$^{-1}$ [νC=C]. $^1H$ NMR ($CD_3CN$, δ/ppm relative to TMS): 8.37 (m, 2H), 7.35 (dd, 2H), 7.33 (dd, 2H), 4.10 (t, 4H), 3.82 (s, 8H), 2.16 (s, 1H), 1.84 (m, 6H), 1.30 (m, 3H).

$(CH_2)_5(MIPF_6)_2$: IR (KBr plate): 3171 and 3126 [ν(C—H) aromatic]; 2953 and 2873 [ν(C—H) aliphatic]; 1618, 1578 and 1474 cm$^{-1}$ [νC=C]. $^1H$ NMR ($CD_3CN$, δ/ppm relative to TMS): 8.36 (m, 2H), 7.35 (dd, 2H), 7.33 (dd, 2H), 4.10 (t, 4H), 3.82 (s, 8H), 2.17 (s, 1H), 1.84 (m, 6H), 1.29 (m, 3H).

Ten Methylene Spacer Group (1,10 Decane):

$(CH_2)_{10}(MIBr)_2$: IR (KBr plate): 3141, 3082 and 3047 [ν(C—H) aromatic]; 2923 and 2848 [ν(C—H) aliphatic]; 1642, 1573 and 1474 cm$^{-1}$ [νC=C]. $^1H$ NMR ($CD_3CN$, δ/ppm relative to TMS): 9.25 (m, 2H), 7.49 (dd, 2H), 7.42 (dd, 2H), 4.19 (t, 4H), 3.88 (s, 6H), 2.75 (s, 1H), 1.83 (m, 4H), 1.29 (m, 16H).

$(CH_2)_{10}(MIBeti)_2$: IR (KBr plate): 3156, 3121 and 3102 [ν(C—H) aromatic]; 2933 and 2868 [ν(C—H) aliphatic]; 1578 and 1469 cm$^{-1}$ [νC=C]. $^1H$ NMR ($CD_3CN$, δ/ppm relative to TMS): 8.38 (m, 2H), 7.36 (dd, 2H), 7.34 (dd, 2H), 4.11 (t, 4H), 3.83 (s, 6H), 2.16 (s, 1H), 1.96 (m, 1H), 1.82 (m, 2H), 1.31 (m, 12H).

$(CH_2)_{10}(MIPF_6)_2$: Anal. Found (calculated): C, 36.60 (36.37); H, 5.42 (5.43); N, 9.40 (9.43). IR (KBr plate): 3171 and 3121 [ν(C—H) aromatic]; 2933 and 2864 [ν(C—H) aliphatic]; 1622, 1578 and 1464 cm$^{-1}$ [νC=C]. $^1H$ NMR ($CD_3CN$, δ/ppm relative to TMS): Due to the long carbon chain and the variety of conformations, there are two peaks caused by the a/a' protons; 8.38 (m, 2H), 7.36/7.36 (dd, 2H), 7.34/7.33 (dd, 2H), 4.11/4.11 (t, 4H), 3.83/3.82 (s, 6H), 2.16/2.15 (s, 1H), 1.96/1.96 (m, 1H), 1.82/1.82 (m, 1H), 1.31 (s, 7H)

$^1H$ NMR was recorded on a 300 Mhz spectrometer and IR spectra were recorded on a Nicolet Impact 400D FTIR spectrophotometer.

EXAMPLE 2

Thermal Stability and Phase Transitions

By replacing the halide anion with the Imide, Beti, or PF6 anion of the CnX salts improved thermal stability is obtained. In addition, lower melting points and lower glass transitions are obtained with these anions compared to that observed with the halides. For example, if we compare the [1,4-bis-(3-methylimidazlium)butane]$^{2+}$2Br$^-$ disclosed by Murphy (WO 00/32658), labeled C4Br in our notation, one would expect a thermal decomposition around 310° C. based on that observed for other analogous bisimidazolium halide salts. In contrast, when the anions such as PF$_6$, Imide, and Beti disclosed in this invention are used, improved thermal stability, above 400° C., is observed. A further advantage of using the organic anions (e.g. Imide or Beti) over the inorganic anions such as PF$_6$ is the lack of HF formation at elevated temperatures. With PF$_6$ HF formation is observed even at 65° C.

Further advantages of the non-halogen containing salts are the lower melting points. In fact, many of the Imide and Beti bisimidazolium salts are liquids at room temperature. For example, the C10Br has a melting point of 148° C. while the C10PF$_6$ salt has a lower melting point of 71° C. and the Beti analog is liquid at room temperature. The advantages of this invention allow one to accurately select the desired phase transition temperatures and improve the thermal stability of the biscationic salts. As demonstrated here, these salts can be classified as Ionic Liquids due to their low melting temperatures. By increasing the length of the connecting group between the cyclic stabilized cationic structure one can tune the phase transition temperature. For example, with a short three carbon methylene linking group (C3 in our notation) the PF$_6$ dication salt has a melting point of 144° C. and the Beti analog is also a solid at room temperature. Increasing the length of the methylene linking group to ten carbons (C10 in our notation) results in the PF$_6$ salt melting point to decrease to 71° C. and the Beti analog to be a liquid at room temperature.

| 1, ω-Bismethyl-imidazolium structure | Room Temperature Phase | Decomposition temperature (° C.) and if decomposition is endo or exothermic | Melting point, freezing point, glass transition |
|---|---|---|---|
| C2Br | solid | 331 endo | mp234, fp104 |
| C2Cl | solid | | |
| C3Br | solid | | |
| C5Br | solid | 310 endo | mp 144, gt 11 |
| C5Cl | solid | 300 endo | mp 77, gt −29 |
| C10Br | solid | 301 endo | mp 148 |
| C3PF6 | solid | 439 endo | mp144, fp79 |
| C3Beti | solid | | |
| C5Im | liquid | 482 exo | gt−55.4 |
| C5PF6 | solid | | |
| C5Beti | liquid | | |
| C10PF6 | solid | 447 endo | mp71, gt−21 |
| C10Beti | liquid | 439 exo | fp−119, gt−51 |

As can be seen from the above table, the compounds having the anions PF$_6$, Beti and Im are significantly better in thermal stability (i.e., have a much higher decomposition temperature).

A Mettler DSC821 and TGA850 were used to obtain thermochemical data. Differential Scanning Calorimetry (DSC) data was obtained in a sealed aluminum pan (prepared in a dry box), with a cooling and heating rate of 10° C./min. Thermal Gravimetric Analysis (TGA) data was obtained in an alumina pan at 20° C./min under N$_2$.

EXAMPLE 3

Electrochemical Stability

| 1, ω-Bismethylimidazolium structure | Window | neg limits | pos limits |
|---|---|---|---|
| C3PF6 | 4.4V | −1.7 | 2.7 |
| C3Beti | 5.5V | −1.9 | 3.6 |
| C5Im | 4.7V | −2.3 | 2.4 |
| C5PF6 | 4.6V | −2 | 2.6 |
| C10PF6 | 4.6V | −2.1 | 2.5 |
| C10Beti | 4.9V | −2.3 | 2.6 |

Electrolyte preparation and work was performed in a Vacuum Atmospheres Corporation dry box (<10 ppm H$_2$O and O$_2$) under an Ar atmosphere. All samples were dried prior to use (45° C., μm vacuum, 24 hours). Conductivity measurements were performed using a General Radio 1656 Impedance Bridge with an Orion conductivity cell having a nominal cell constant of 1 (conductivity cells were calibrated with a KCl solution). Variable temperature data was obtained from a sealed cell in a Tenney environmental chamber. The conductivity values obtained going down in temperature agreed with those collected going up in temperature. Cyclic voltammetry results were obtained with a freshly polished glassy carbon disk working electrode (0.077 cm$^2$) and a high surface area (26 m$^2$) carbon counter electrode. An EG&G 272A Potentiostat/Galvanostat was used at a scan rate of 20 mV/s. A silver (Ag) wire served as a quasi-reference electrode, poised at approximately 3 V vs. Li/Li$^+$. All reported voltages for cathodic or anodic limits are at current densities of 20 μA/cm$^2$. Viscosity was determined with a Brookfield cone plate viscometer (range: 0.3–1,000 cP), equipped with a Neslab recirculating bath (−15 to 120° C.).

EXAMPLE 4

Biphase Hydroformylation with 1,10-bis(3-Methylimidazolium)decane(PF$_6$)$_2$ (C10PF$_6$) as the Solvent Using a 1L pressure reactor (Parr), the hydroformylation of the terminal olefin is performed. We investigated 1-pentene and 1-octene hydroformylation. To the 1 L bomb a catalyst of dicarbonylacetylacetonate rhodium (II) (Rh (CO)$_2$ acac; (0.300 mmole) and triphenylphosphine (2.69 mmole) is added to 10 grams of the 1,10-bis(3-methylimidazolium)decane (PF$_6$)$_2$ (C10PF$_6$). Before sealing the reactor, 30 ml of the olefin, either 1-pentene or 1-octene is added. Once the bomb is sealed, it is flushed with CO/H$_2$ gas. The bomb is then pressurized to 80 psi and is not allowed below this pressure by using a check valve. The reactor is heated and stirred for the required time (e.g. 2 hours at 80° C.), followed by cooling to room temperature. The aldehydes were decanted off. Typical conversions of greater that 95% are obtained with a terminal aldehyde to branched aldehyde distribution of greater than 3:1 being obtained. For example 80% hexanol and 20% 2-methyvaleraldehyde is obtained from 1-pentene. The remaining C10PF6/catalyst phase may be recharged with olefin for repetitive hydroformylation reactions. More than 10 cycles were obtained with less than 1% loss in catalytic activity.

EXAMPLE 5

Usage of the Salts Discovered Herein

The salts invented herein are well suited for numerous applications requiring high thermal and electrochemical stability, good ionic conductivity, selective lyophobicity and selective viscocity. These salts are used instead of the common materials previously used in these applications. For example, in batteries and other electrochemical storage devices (supercapacitors and lithium ion batteries), these materials may be used as electrolytes. For gas turbine and and other high temperature lubricating applications requiring low-coking, high thermal stability lubricants, these salts can be used. They find usage as replacement for solvents used as extraction and reaction media. They can also be used as replacements for electrolytes used in electroluminescent and electrochromic devices. By selecting the anion and cation structure properly, these materials can be designed for optimum performance.

Those with expertise in this field will recognize variations in the invention which are consistent with the disclosure herein.

What is claimed is:

1. A salt comprising two or more delocalized cations, said cations being separated by spacer groups, wherein said cations are selected from the group consisting of:

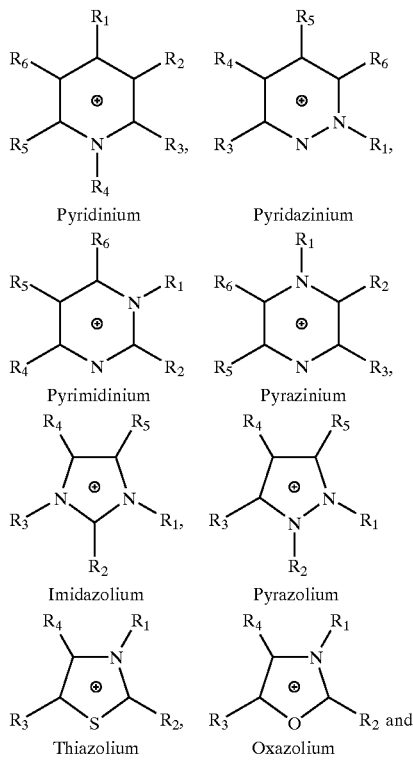

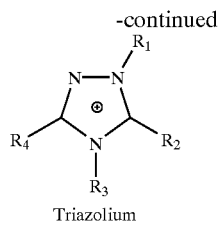

Triazolium wherein $R_1$, $R_2$, $R_3$, $R_4$, $R_5$, and $R_6$ are either H, F, or separate alkyl groups having 1–25 carbon atoms; or any two of $R_1$–$R_6$ can be joined together to constitute a unitary alkylene radical forming one or more ring structures converging on the cyclic delocalized aromatic ring; and wherein the alkyl groups or alkylene radicals may be substituted with electron withdrawing groups; and wherein said salt also comprises anions in appropriate number to maintain charge neutrality, and wherein said anion is a polyatomic anion having a van der Waals volume exceeding 100 $A^3$.

2. The salt of claim 1 wherein said salt is hydrophobic.
3. The salt of claim 1 wherein said salt is hydrophilic.
4. The salt of claim 1 wherein all cations are the same.
5. The salt of claim 1 which comprises 2 or more different cations.
6. The salt of claim 1 wherein said spacer groups contain from one to thirty-five repeating units having saturated or unsaturated bonds.
7. The salt of claim 1 wherein said spacer groups contain inorganic atoms.
8. The salt of claim 1 wherein said anions are connected to each other resulting in separate linear chains of anions and cations.
9. The salt of claim 1 wherein said anions are connected in a tethered fashion to the linear cation chain.
10. The salt of claim 1 wherein said anions are selected from the group consisting of $PF_6$, Im, Beti, BAI, TAM and Me.
11. The salt of claim 1 wherein said cation comprises alkyl groups at all non-linking positions, said alkyl groups containing 1–25 carbon atoms.
12. The salt of claim 1 wherein said salt is a zwitterion.
13. A process for using the salt of claim 1, said process comprising adding said salt to a device selected from the group consisting of electrochemical storage devices, electroluminescent devices and electrochromic devices to serve as the electrolyte of said device.

* * * * *

UNITED STATES PATENT AND TRADEMARK OFFICE
CERTIFICATE OF CORRECTION

PATENT NO. : 6,531,241 B1
DATED : March 11, 2003
INVENTOR(S) : Alan B. McEwen

It is certified that error appears in the above-identified patent and that said Letters Patent is hereby corrected as shown below:

Column 7,
Line 3, "PF6" should read -- $PF_6$ --; and

Column 10,
Line 21, "$A^3$" should read -- $Å^3$ --.

Signed and Sealed this

Twenty-fifth Day of May, 2004

JON W. DUDAS
*Acting Director of the United States Patent and Trademark Office*